United States Patent [19]

Chen

[11] Patent Number: 5,488,763
[45] Date of Patent: Feb. 6, 1996

[54] METHOD FOR MAKING A MOLD FOR A LENS OF SINGLE LENS GLASSES HAVING TWO FOCAL AXES

[76] Inventor: Chin-Jen Chen, No. 22-9, Liu Kuai Liao, Liu Chia Village, An Ting Hsiang, Tainan Hsien, Taiwan

[21] Appl. No.: 226,351

[22] Filed: Apr. 12, 1994

[51] Int. Cl.$^6$ .................................................. B29D 11/00
[52] U.S. Cl. ............................. 29/407; 29/557; 264/2.1; 264/2.5; 425/808
[58] Field of Search ............................. 264/1.7, 1.8, 2.5, 264/2.1; 425/808; 29/407, 557

[56] References Cited

U.S. PATENT DOCUMENTS

| | | |
|---|---|---|
| 3,109,696 | 11/1963 | Whitney . |
| 3,460,928 | 8/1969 | Casko ....................................... 264/2.5 |
| 3,555,126 | 1/1971 | Gitson . |
| 4,338,672 | 5/1983 | Kreuttner ................................. 425/808 |
| 4,906,422 | 3/1990 | Buckley .................................... 264/2.5 |
| 5,147,585 | 9/1992 | Blum ......................................... 264/1.7 |
| 5,252,056 | 10/1993 | Horner et al. ........................... 425/808 |

*Primary Examiner*—Mathieu D. Vargot
*Attorney, Agent, or Firm*—Morton J. Rosenberg; David I. Klein

[57] ABSTRACT

A method for making a mold for forming a lens for single lens glasses having two focal axes is provided. The mold consists of a male mold and a female mold. The male mold is made from portions of two conventional male molds to provide a left half portion and a right half portion of a new male mold, each portion having a separate focal axis. Subsequently the left and the right half portions are jointed together to be used with a conventional female mold to produce a lens for single lens glasses having two focal axes.

1 Claim, 7 Drawing Sheets

---

PREPARE TWO CONVENTIONAL MALE MOLDS FOR MAKING A LENS OF SINGLE LENS GLASSES HAVING A SINGLE FOCAL AXIS.

↓

PUT ONE OF THE CONVENTIONAL MALE MOLDS TOGETHER WITH A FEMALE MOLD, ROTATE THE MALE MOLD RELATIVE TO THE FEMALE MOLD TO MOVE THE FOCAL AXIS LINE TO INTERSECT A LEFT END POINT ON THE FEMALE MOLD, THE DISTANCE CORRESPONDING TO THE DISTANCE BETWEEN THE PUPILS OF A PERSON'S EYES, AND CUT OFF A LEFT PORTION (22) FORMED BY A HORIZONTAL SIDE AND A VERTICAL CENTER LINE OF THE FEMALE MOLD.

↓

PUT THE OTHER CONVENTIONAL MALE MOLDS TOGETHER WITH A FEMALE MOLD, ROTATE THE MALE MOLD RELATIVE TO THE FEMALE MOLD TO MOVE THE FOCAL AXIS LINE TO INTERSECT A RIGHT END POINT ON THE FEMALE MOLD, THE DISTANCE CORRESPONOING TO 1/2 THE DISTANCE BETWEEN THE PUPILS OF A PERSON'S EYES, AND CUT OFF A RIGHT PORTION (42) FORMED BY A HORIZONTAL SIDE AND A VERTICAL CENTER LINE OF THE FEMALE MOLD.

↓

JOIN TOGETHER THE LEFT PORTION AND THE RIGHT PORTION, MAKING A NEW MALE MOLD FOR FORMING A LENS OF SINGLE LENS GLASSES WITH TWO FOCAL AXES.

PREPARE TWO CONVENTIONAL MALE MOLDS FOR MAKING A LENS OF SINGLE LENS GLASSES HAVING A SINGLE FOCAL AXIS.

PUT ONE OF THE CONVENTIONAL MALE MOLDS TOGETHER WITH A FEMALE MOLD, ROTATE THE MALE MOLD RELATIVE TO THE FEMALE MOLD TO MOVE THE FOCAL AXIS LINE TO INTERSECT A LEFT END POINT ON THE FEMALE MOLD, THE DISTANCE CORRESPONDING TO THE DISTANCE BETWEEN THE PUPILS OF A PERSON'S EYES, AND CUT OFF A LEFT PORTION (22) FORMED BY A HORIZONTAL SIDE AND A VERTICAL CENTER LINE OF THE FEMALE MOLD.

PUT THE OTHER CONVENTIONAL MALE MOLDS TOGETHER WITH A FEMALE MOLD, ROTATE THE MALE MOLD RELATIVE TO THE FEMALE MOLD TO MOVE THE FOCAL AXIS LINE TO INTERSECT A RIGHT END POINT ON THE FEMALE MOLD, THE DISTANCE CORRESPONOING TO 1/2 THE DISTANCE BETWEEN THE PUPILS OF A PERSON'S EYES, AND CUT OFF A RIGHT PORTION (42) FORMED BY A HORIZONTAL SIDE AND A VERTICAL CENTER LINE OF THE FEMALE MOLD.

JOIN TOGETHER THE LEFT PORTION AND THE RIGHT PORTION, MAKING A NEW MALE MOLD FOR FORMING A LENS OF SINGLE LENS GLASSES WITH TWO FOCAL AXES.

METHOD FOR MAKING A MOLD FOR A LENS OF SINGLE LENS GLASSES HAVING TWO FOCAL AXES

BACKGROUND OF THE INVENTION

Single lens glasses are widely used for sports and industry, such single lens glasses closely cover the two eyes of a user. The conventional mold for producing prior art single focus single lens glasses is shown in FIG. 7. The conventional mold comprises a male mold 11 and a female mold 12, each respectively having a different radius for use in a plastic injecting process, where plastic is injected into the space between the molds. The single lens glasses have a single central point 13 where the lens is the thickest.

These type of single lens glasses are used for sports and in industry and function to protect human eyes, but it easily makes the user's eyes tired if such glasses are worn for a long period of time. Most of the people who use these glasses have experienced the problem. The problem is caused by the fact that the lens only has a single focal axis which is centrally located, instead of two focal axes displaced from one another by a distance corresponding to the distance between the pupils of a person's two eyes, normally about 65–68 mm. That is the reason why the single lens glasses cannot enable human eyes to still feel comfortable after wearing such glasses for a long period of time.

SUMMARY OF THE INVENTION

In view of the disadvantage of conventional single lens glasses for sports and industry, this invention has been devised to offer a method for making a mold for injection molding of a lens for single lens glasses having two focal axes.

A mold in the present invention consists of a male mold and a female mold put together for plastic material to be injected between a narrow space formed by the male and the female mold, to form a lens of single lens glasses with two focal axes.

The male mold is made from two conventional molds used in manufacturing conventional lenses for single lens glasses with a single focal axis, by cutting off unnecessary portions of the two molds to thereby make a left half portion and a right half portion of a new male mold. The left half portion is made by rotating one of the conventional male molds relative to the female mold, positioning an upper point of the focal axis line of the male mold to a left end point, equivalent to half the distance between the pupils of a person's two eyes. Then, the portion of the male mold extending between the original horizontal side thereof and the vertical center line of the female mold is removed, as is the portion extending beyond the horizontal end of the female mold, thereby forming the left half portion of the new male mold. The right half portion is made in a similar way, by rotating another conventional male mold relative to the female mold, positioning the upper point of the focal axis line to a right end point corresponding to half the distance between the pupils of a person's two eyes. As was done for the left half, the portion of the male mold extending between the original horizontal side thereof and the vertical center line of the mold and the portion extending beyond the horizontal end of the female mold are removed. After that, the two half portions are firmly joined together to form a new male mold to be used with the existing conventional female mold.

BRIEF DESCRIPTION OF THE DRAWINGS

The invention will be better understood by reference to the accompanying drawings, wherein:

FIG. 1 is a flow chart of method of making a mold for making a lens of single lens glasses with two focal axes according to the present invention;

DESCRIPTION OF THE PREFERRED EMBODIMENTS

A method for making a mold for a lens of single lens glasses having two focal axes is shown in the flow chart of FIG. 1.

A first step is to prepare two conventional male molds 2 for making lenses for glasses having a single focal axis.

Figure 2:
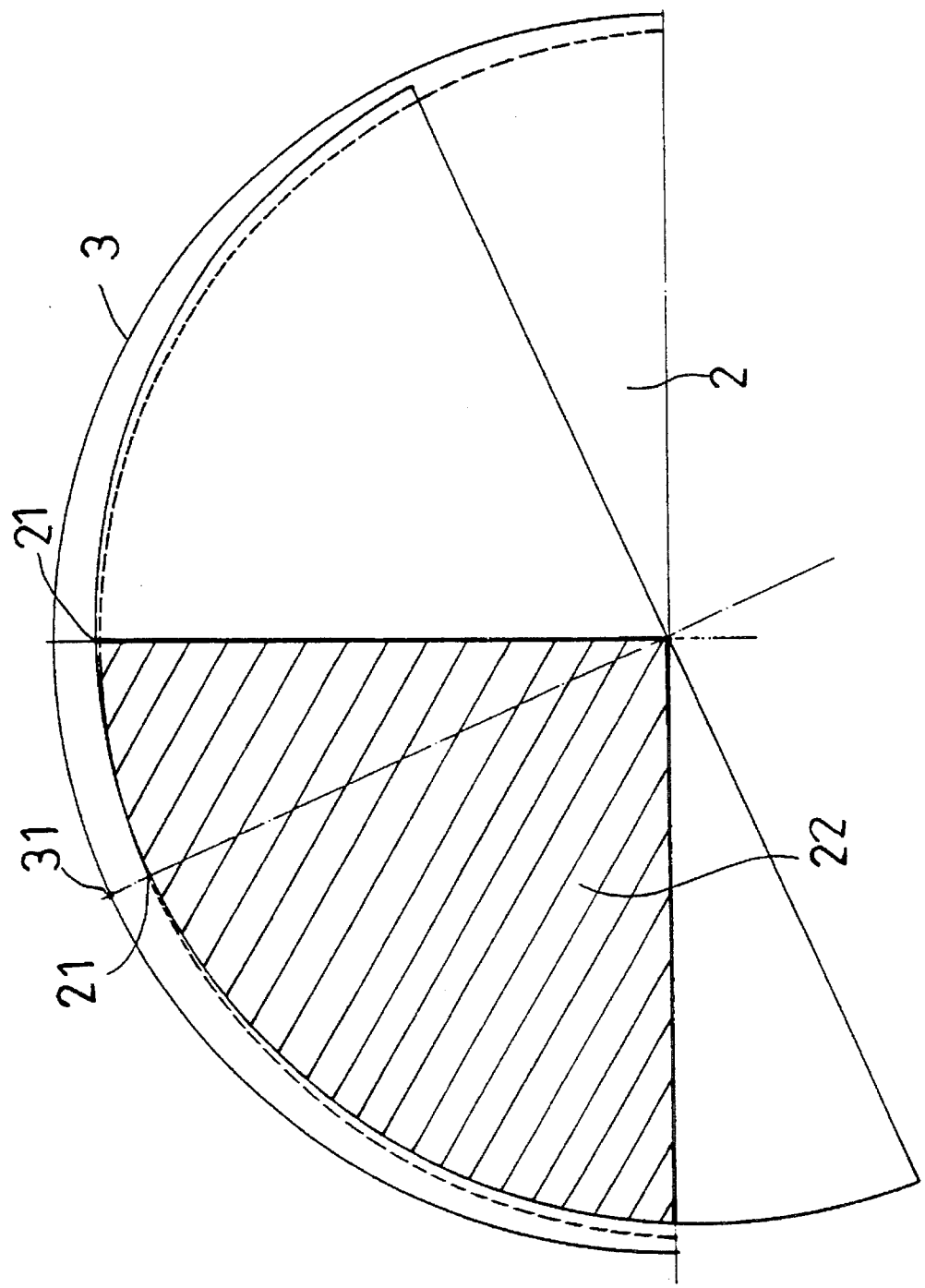
FIG. 2 is a cross-sectional diagrammatic view of the second step in the method of the present invention.

A second step, as shown in FIG. 2, is to determine an upper point 31 for intersection of the focal axis line 21 of one of the conventional male molds 2 and to rotate this mold 2 relative to the conventional female mold 3 to move the focal axis line 21 to intersect the selected left end point 31 on the female mold 3, the distance rotated corresponding to half the distance between the centers of the pupils of a person's two eyes. Subsequently, the unnecessary portions, shown as non-cross-hatched areas, are cut off to leave the portion 22, marked with cross-hatching. The portion 22 then becomes a left half portion of a new male mold 5 with a focal axis 21 intersecting a point 31.

Figure 3:
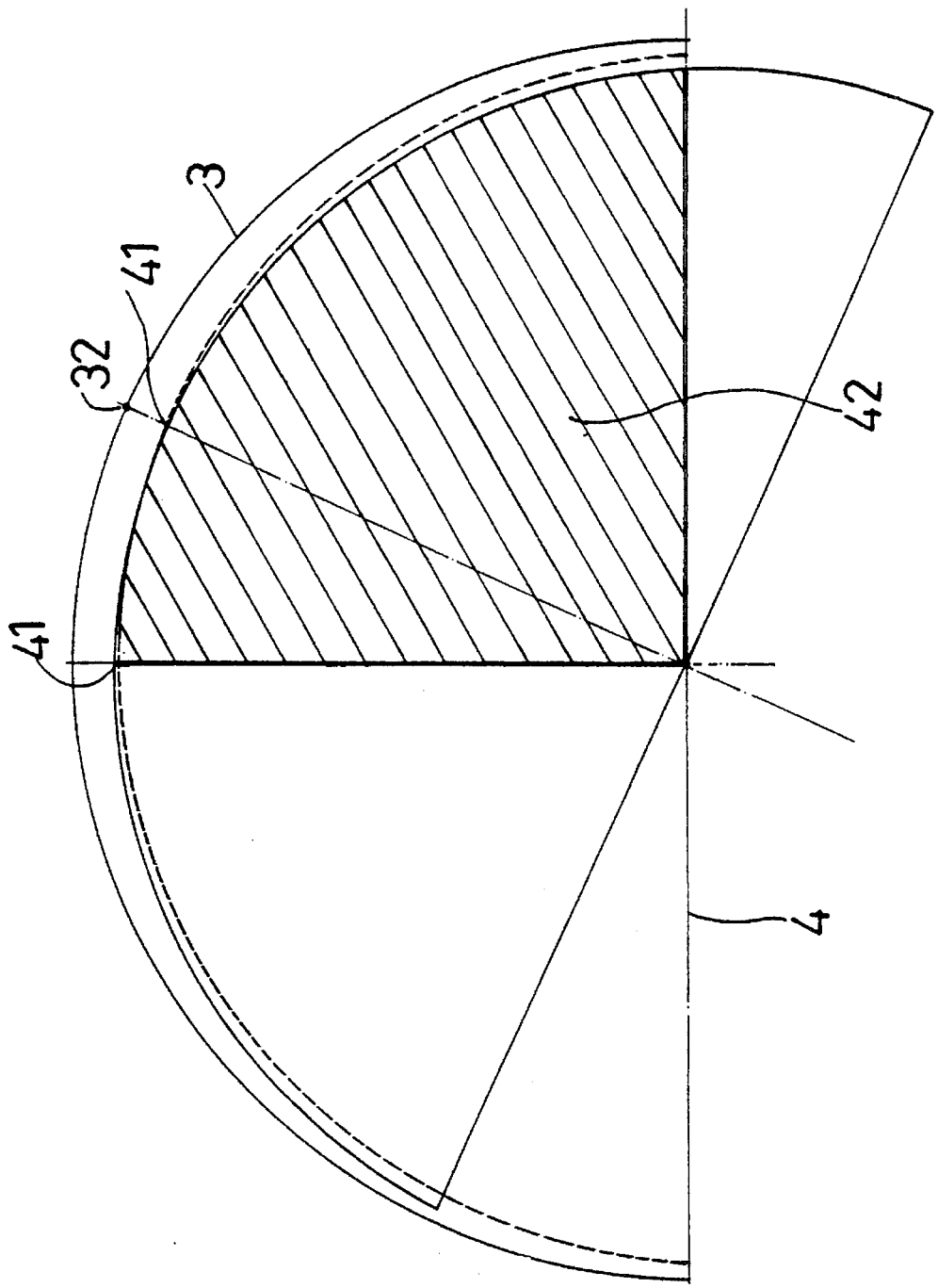
FIG. 3 is a cross-sectional diagrammatic view of the third step in the method of the present invention.

A third step, as shown in FIG. 3, is to determine an upper point 32 for intersection of the focal axis line 41 of the other male mold 2 and to rotate this mold 2 to move the focal axis line 41 to intersect the selected right end point 32 on the female mold 3, the distance rotated corresponding to half the distance between the centers of the pupils of a person's two eyes. As in the prior step, the unnecessary portions, shown as non-cross-hatched areas, are cut off to leave the portion 42, marked with cross-hatching. The portion 42 becomes the right half portion of the new male mold 5 with a focal axis 41 intersecting a point 41.

Figure 4:
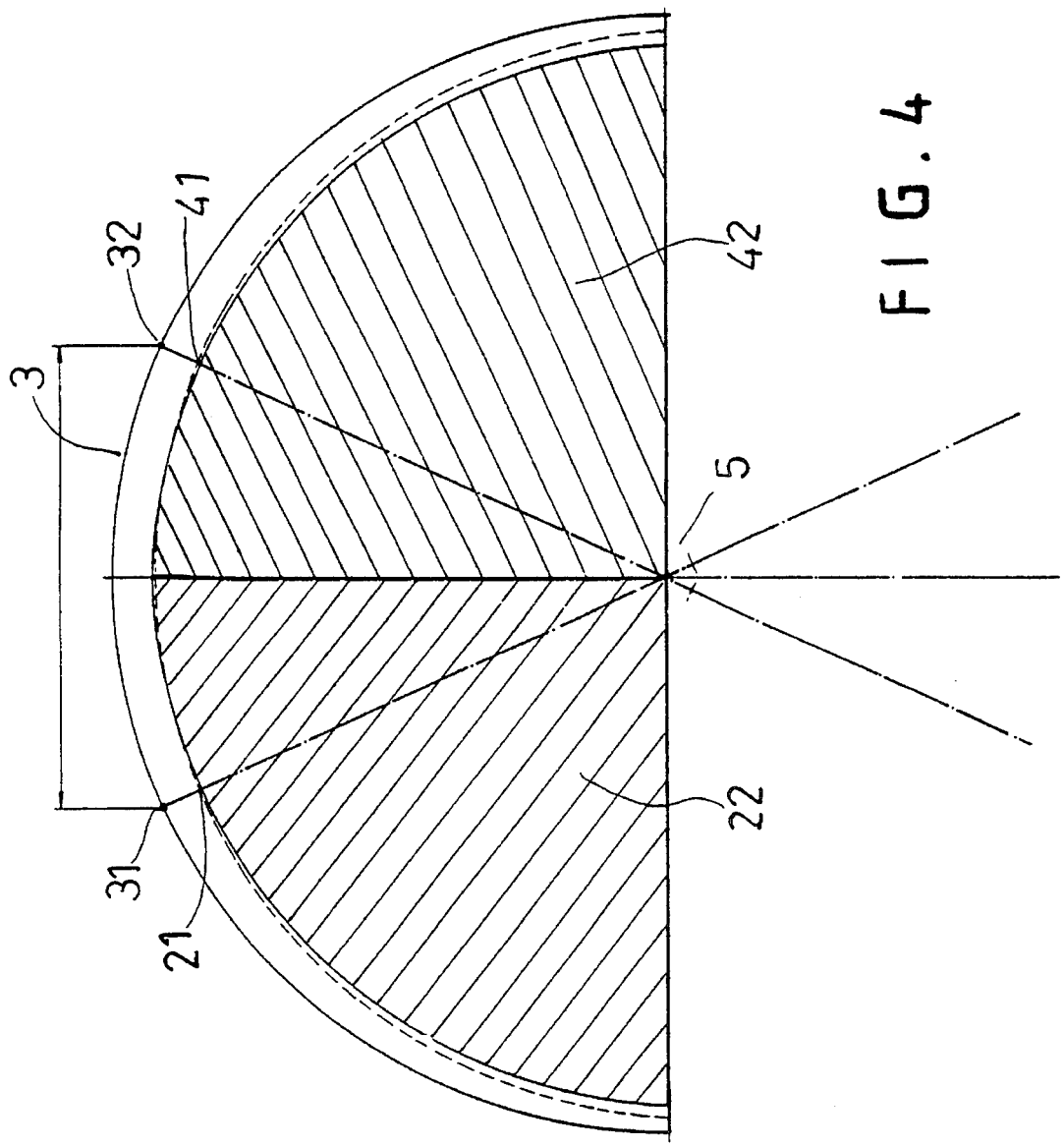
FIG. 4 is a cross-sectional diagrammatic view of the fourth step in the method of the present invention.
Figure 5:
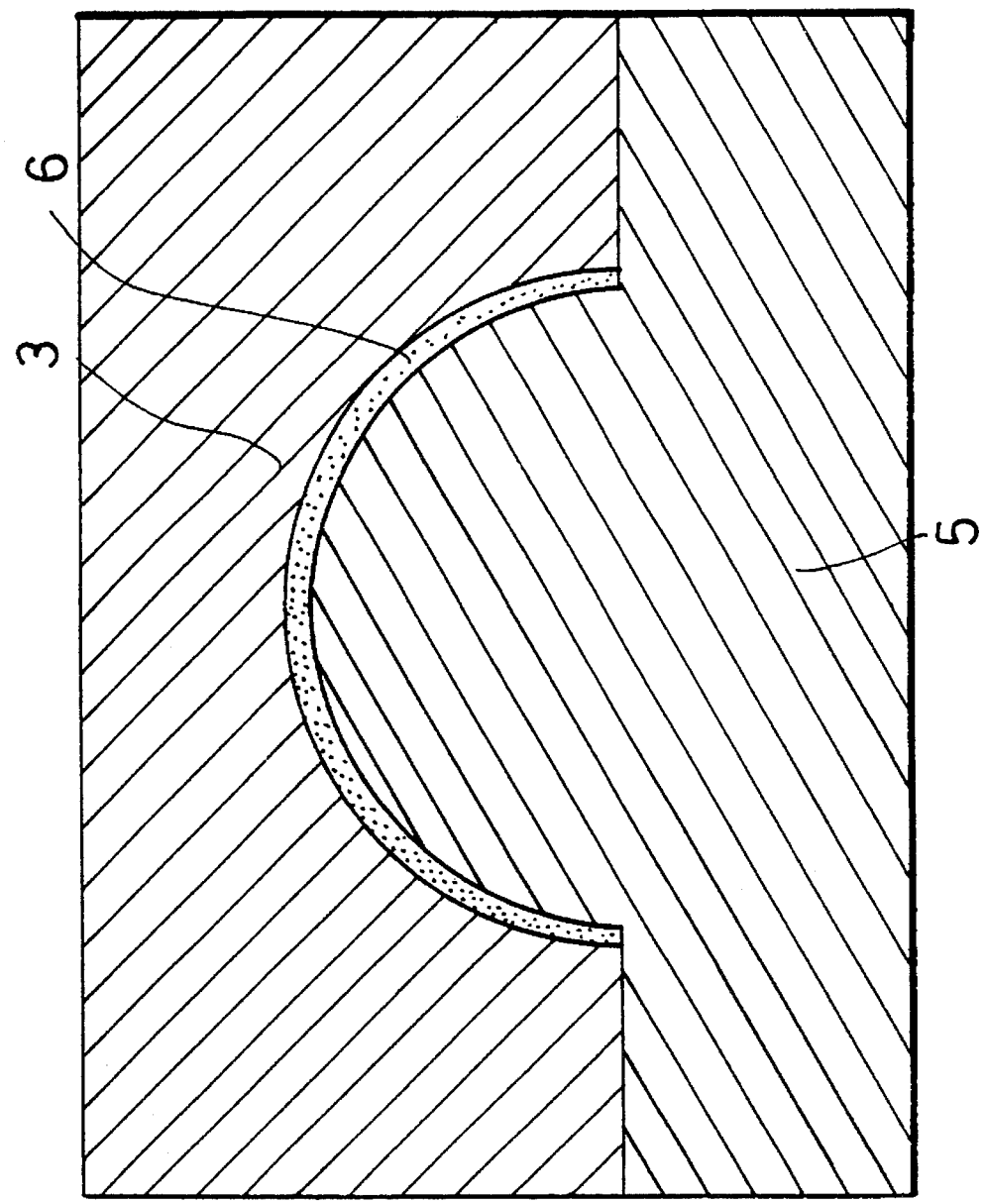
FIG. 5 is a cross-sectional view of a male and a female mold put together for injecting plastic material therebetween to form a lens of single lens glasses with two focal axes according to the method of the present invention.
Figure 6:
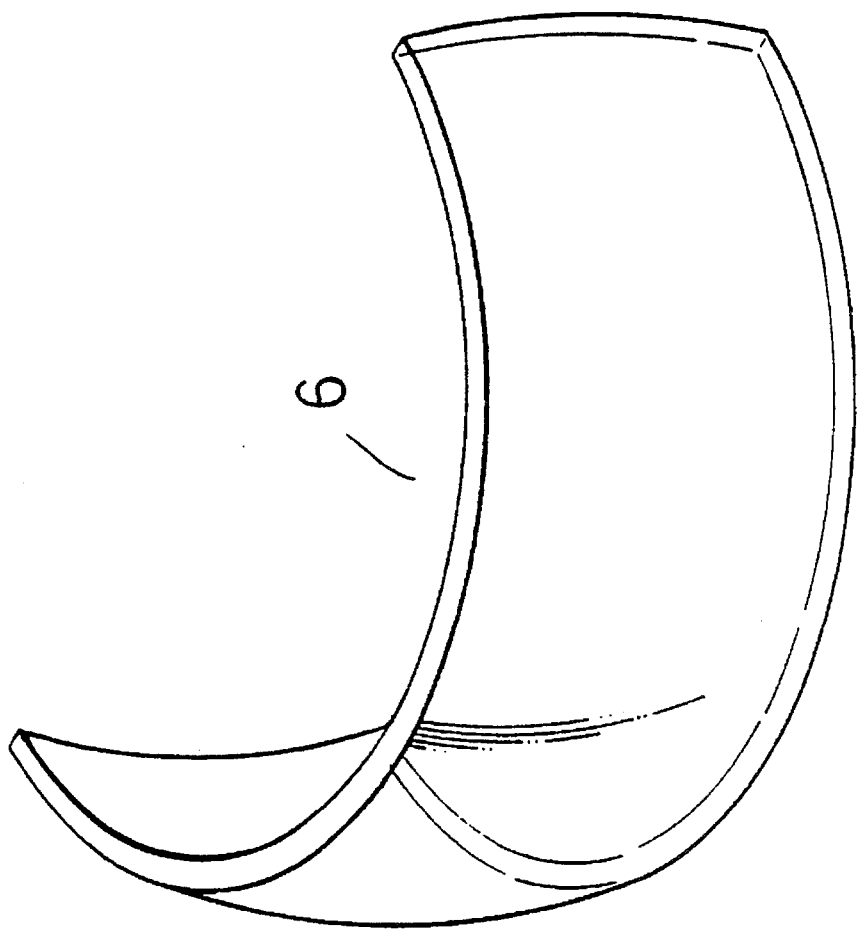
FIG. 6 is a perspective view of a lens of single lens glasses with two focal axes produced by means of the mold made according to the method of the present invention; and, FIG. 7 is a cross-sectional diagrammatic view of a conventional mold for making a lens of single lens glasses with a single focal axis.
Figure 7:
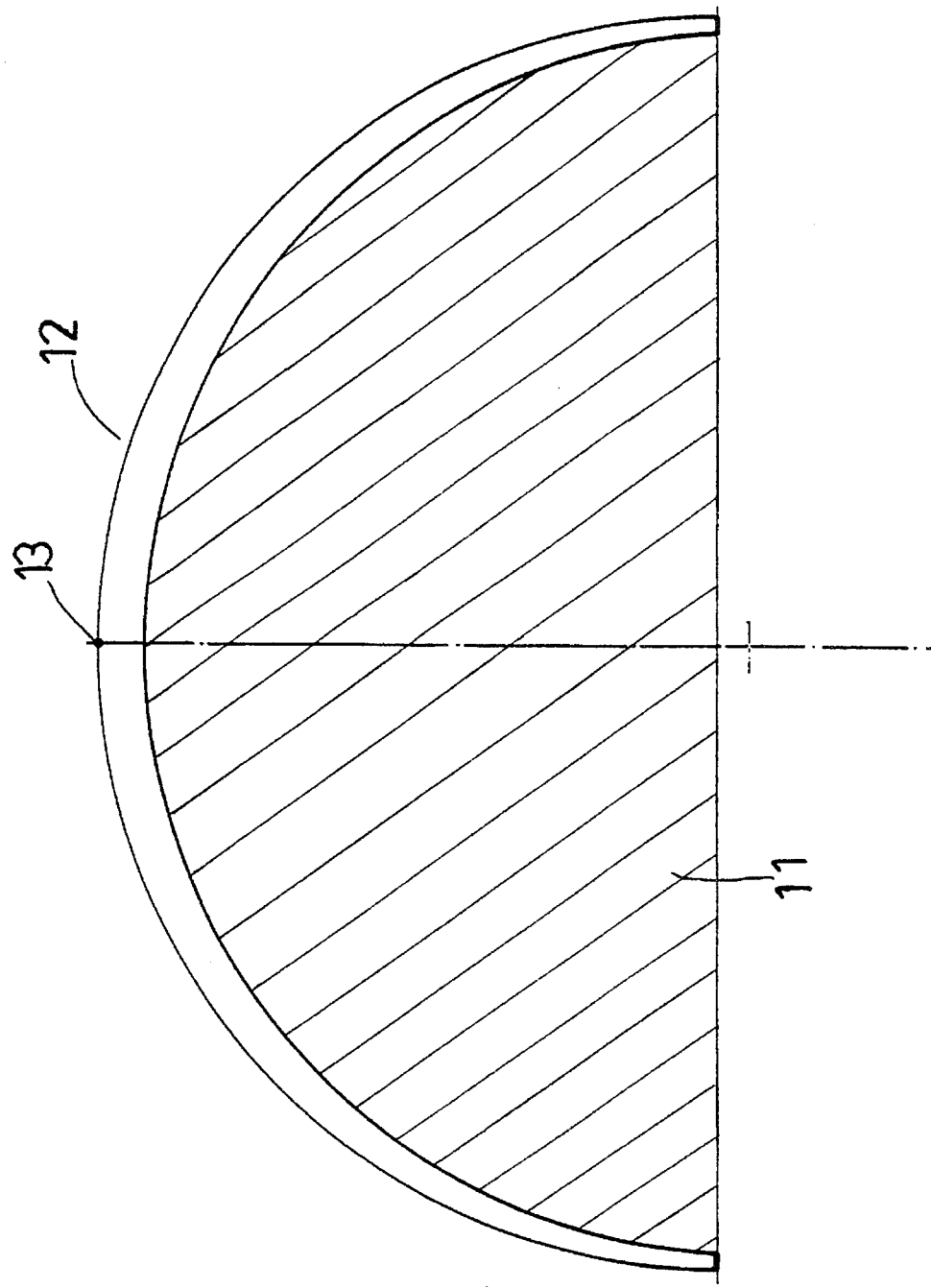

The fourth step, as shown in FIG. 4, is to make a new male mold 5 by firmly joining together the two male half molds 22 and 42 obtained in the second and the third steps by appropriate means. This new male mold 5 is used together with the conventional female mold 3, where plastic is injected in a narrow space formed between the molds 5 and 3 to form a lens of single lens glasses with a glossy surface and having two focal axes.

While the preferred embodiments of the invention have been described above, it will be recognized and understood that various modifications may be made therein and the appended claims are intended to cover all such modifications which may fall within the spirit and scope of the invention.

What is claimed is:

1. A method for making a mold for forming a lens of single lens glasses having two focal axes from molds for forming lenses of single lens glasses with a single focal axis, comprising the steps of:

providing a first male mold and a corresponding female mold for forming a lens for single lens glasses;

b. providing a second male mold for forming a lens for single lens glasses;

c. positioning said first male mold in said female mold and rotating a centrally located focal axis of said first male mold in a first direction a predetermined distance relative to said female mold, said predetermined distance corresponding to approximately one half a person's pupillary distance;

d. cutting out a first segment of said first male mold bounded by a horizontal side and a vertical center line of said female mold;

e. positioning said second male mold in said female mold and rotating a centrally located focal axis of said first male mold in a second direction said predetermined distance relative to said female mold, said second direction being opposite said first direction;

f. cutting out a second segment of said second male mold bounded by said horizontal side and said vertical center line of said female mold;

g. affixing said first segment to said second segment to form a third male mold, said third male mold being insertable into said female mold for forming a lens of single lens glasses having a pair of focal axes spaced one for the other by a pupillary distance.

* * * * *